US009523154B2

(12) United States Patent
Bellenger et al.

(10) Patent No.: US 9,523,154 B2
(45) Date of Patent: Dec. 20, 2016

(54) USE OF PHENOL COMPOUNDS AS ACTIVATOR FOR METAL SURFACE CORROSION

(75) Inventors: Fabien Bellenger, Vossem (BE); Cheng Shen, Shanghai (CN); Claude D. Mercier, Shanghai (CN)

(73) Assignees: SOLVAY (CHINA) CO., LTD., Shanghai (CN); RHODIA OPERATIONS, Paris (FR)

( * ) Notice: Subject to any disclaimer, the term of this patent is extended or adjusted under 35 U.S.C. 154(b) by 159 days.

(21) Appl. No.: 14/366,716

(22) PCT Filed: Dec. 20, 2011

(86) PCT No.: PCT/CN2011/084301
§ 371 (c)(1),
(2), (4) Date: Sep. 5, 2014

(87) PCT Pub. No.: WO2013/091177
PCT Pub. Date: Jun. 27, 2013

(65) Prior Publication Data
US 2015/0005219 A1    Jan. 1, 2015

(51) Int. Cl.
| C23G 1/12 | (2006.01) |
| C23G 1/20 | (2006.01) |
| C23G 1/22 | (2006.01) |
| C11D 7/26 | (2006.01) |
| C11D 7/34 | (2006.01) |
| C11D 11/00 | (2006.01) |
| C07C 39/10 | (2006.01) |
| C07C 65/05 | (2006.01) |

(52) U.S. Cl.
CPC ............... *C23G 1/125* (2013.01); *C07C 39/10* (2013.01); *C07C 65/05* (2013.01); *C11D 7/261* (2013.01); *C11D 7/265* (2013.01); *C11D 7/34* (2013.01); *C11D 11/0029* (2013.01); *C23G 1/20* (2013.01); *C23G 1/22* (2013.01)

(58) Field of Classification Search
CPC .................................................. C11D 11/0047
See application file for complete search history.

(56) References Cited

U.S. PATENT DOCUMENTS

| 3,468,920 A | 9/1969 | Larimer |
| 4,437,928 A | 3/1984 | Wong |
(Continued)

FOREIGN PATENT DOCUMENTS

| CN | 1091161 A1 | 8/1994 |
| CN | 1993457 A1 | 7/2007 |
(Continued)

OTHER PUBLICATIONS

Rhodes, F.H. et al.—"Corrosion of metals by phenols", Industrial and Engineering Chemistry, May 1934, vol. 26, No. 5, pp. 533-534 (2 pages).

*Primary Examiner* — Gregory Webb
(74) *Attorney, Agent, or Firm* — Osha Liang LLP

(57) ABSTRACT

Use of a compound of Formula (I) as a metal surface corrosion activator, a formulation containing the same compound and a process by using the same compound for providing a clean metal surface. Said formulation may further comprise water, a solvent such as a dipolar aprotic solvent, a water miscible organic solvent, or an organic base.

20 Claims, 3 Drawing Sheets

(56) References Cited

U.S. PATENT DOCUMENTS

| | | |
|---|---|---|
| 5,911,835 A | 6/1999 | Lee et al. |
| 6,110,881 A | 8/2000 | Lee et al. |
| 6,319,885 B1 | 11/2001 | Lee et al. |
| 7,051,742 B2 | 5/2006 | Lee et al. |
| 7,144,849 B2 | 12/2006 | Lee et al. |
| 2005/0029490 A1* | 2/2005 | Subawalla ............... C11D 1/72 252/79 |
| 2006/0189141 A1 | 8/2006 | Mahlkow et al. |
| 2007/0087949 A1 | 4/2007 | Wu et al. |
| 2008/0051308 A1 | 2/2008 | Kane |
| 2009/0224204 A1 | 9/2009 | Marion et al. |
| 2009/0291873 A1* | 11/2009 | Tamboli ............... C11D 3/2075 510/175 |
| 2011/0195890 A1 | 8/2011 | Abbas |

FOREIGN PATENT DOCUMENTS

| | | |
|---|---|---|
| CN | 101285193 A | 10/2008 |
| JP | S60-050182 A | 3/1985 |
| JP | H02-250986 A | 10/1990 |
| JP | H10-251874 A | 9/1998 |
| JP | 2000-219978 A | 8/2000 |
| JP | 2002-121598 A | 4/2002 |
| JP | 2004-067846 A | 3/2004 |
| JP | 2006-521464 A | 9/2006 |
| JP | 2007-128064 | 5/2007 |
| WO | WO 2006/023061 A1 | 3/2006 |
| WO | WO 2007/101929 A1 | 9/2007 |
| WO | 2010/043796 A1 | 4/2010 |

* cited by examiner

USE OF PHENOL COMPOUNDS AS ACTIVATOR FOR METAL SURFACE CORROSION

This application is a U.S. national stage entry under 35 U.S.C. §371 of International Application No. PCT/CN2011/084301 filed Dec. 20, 2011.

TECHNICAL FIELD

The present invention generally relates to metal surface treatment permitting to clean or polish surface by an activation of the metal surface treatment.

BACKGROUND OF THE INVENTION

Traditionally, phenol compounds such as catechol (PC) have been used as metal corrosion inhibitors. Examples of metal corrosion inhibitors reported in literature include: t-butylcatechol, pyrogallol, benzotriazole (BZT), resorcinol, esters of gallic acid and mixtures thereof. These are non-free acid functionality corrosion inhibitors which avoid corrosion of metals. In patents of U.S. Pat. No. 5,911,835, U.S. Pat. No. 6,110,881, U.S. Pat. No. 6,319,885, U.S. Pat. No. 7,051,742, and U.S. Pat. No. 7,144,849, dihydroxy aromatic corrosion inhibitors such as catechol are used as metal corrosion inhibitors.

WO2006/023061 discloses a formulation as a stripping and cleaning composition for cleaning microelectronics substrate "without any significant aluminium corrosion" (page 2 [0004]). Again, phenol compounds such as catechol are included in the formulation for the purpose of preventing metal corrosion.

There is always a need for new method of metal surface treatment and providing clean metal surface.

BRIEF SUMMARY OF THE INVENTION

The present invention is based on a new finding that phenol compounds can be used as an activator for metal surface corrosion. Said compounds permit to provide a metal surface treatment activation, notably useful to prevent or decrease further appearances of corrosion on the metal surface.

In one aspect, the present invention provides use of a compound of Formula (1) as a metal surface corrosion activator,

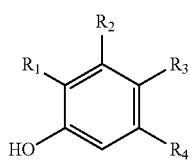

Formula (1)

wherein each of $R_1$, $R_2$ and $R_4$ is hydrogen, hydroxyl, alkyl, sulfonic group or carboxylic group; $R_3$ is hydrogen, alkyl, sulfonic group or carboxylic group.

Preferably the compound of Formula (1) is a phenol compound, more preferably the compound of Formula (1) is a diphenol compound, and most preferably the compound of Formula (1) is 2,3-dihydroxy benzoic acid, catechol, 4-methyl catechol or 4-tertio-butyl catechol.

The present invention also relates to use of a compound of Formula (1) as a metal surface corrosion activator in the manufacture of a formulation for metal surface corrosion.

The above compound of Formula (1) is used in a formulation for metal surface corrosion. In said formulation, the compound of Formula (1) is present preferably in an amount of about 0.1% to about 20% by weight of the formulation, and more preferably about 1% to about 5% by weight of the formulation.

In addition to the compound of Formula (1), the formulation further comprises water to form an aqueous solution.

Optionally, the formulation further comprises a solvent, such as a dipolar aprotic solvent; notably to remove organic residues from a metal surface.

Optionally, the formulation further comprises a water miscible organic solvent to form a homogeneous phase.

Optionally, the formulation further comprises an organic base to adjust pH.

In another aspect, the present invention relates to a process of providing a clean metal surface by surface corrosion by using the above compound or the above formulation.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
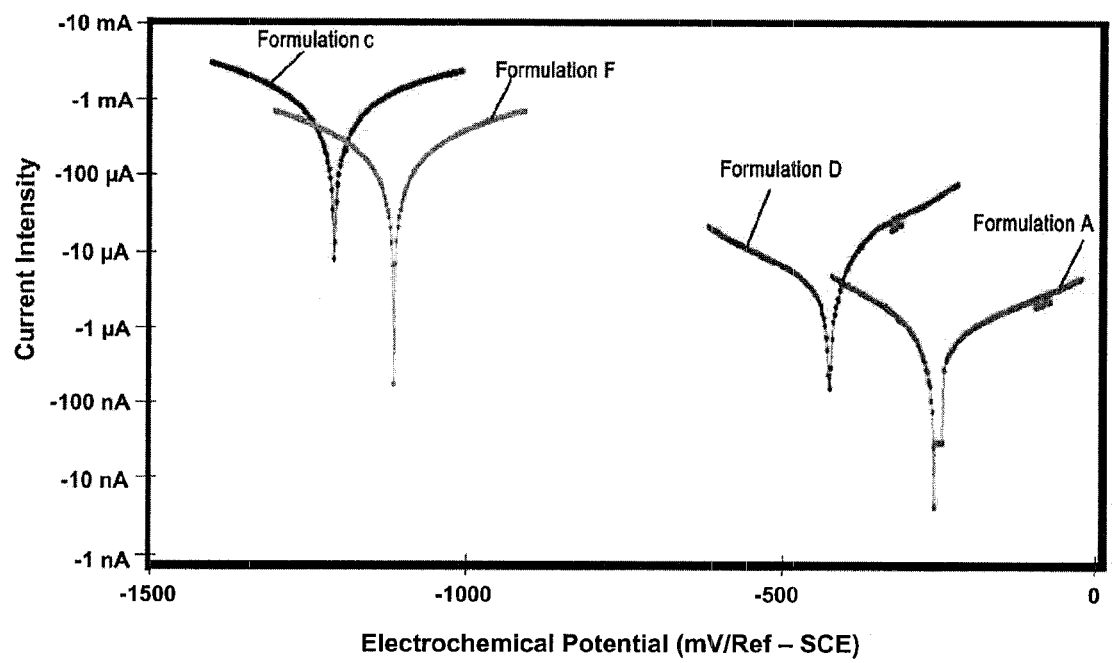
FIG. 1 shows the electro-chemical test results of Al sample obtained with blank (no diphenol additive), Formulations A, C, D and F.

Unless otherwise stated, the following terms used in this application, including the specification and claims, have the definitions given below. It must be noted that, as used in the specification and the appended claims, the singular forms "a" "an" and "the" include plural referents unless the context clearly dictates otherwise. In this application, the use of "or" or "and" means "and/or" unless stated otherwise. Furthermore, use of the term "including" as well as other forms, such as "include", "includes" and "included" is not limiting.

In the practice of manufacture, it is necessary to remove unwanted materials from the surfaces of, for example, metal and/or metal alloy layers, such as the layer of aluminum, copper, titanium, tungsten, and/or alloys thereof, aluminum or metal layer of some objects in the construction area, for example aluminum window frame or metal layer of some electronics devices. In some instances the materials to be removed are organic residues such as resin. In other instances the materials to be removed are simply contaminants. The purpose of surface corrosion in this invention is to remove unwanted materials from a surface layer and to provide a clean metal surface.

It has now been found that a certain phenol compounds suprisingly have the effect of activating metal surface corrosion. By applying the phenol compounds to the metal surface to be treated, a homogeneous corrosion would occur and a clean metal surface will be resulted in by removing the superficial layer of the metal together with any organic residues on the metal superficial layer.

The phenol compounds useful as a metal surface corrosion activator of the present invention are as defined in the above identified Formula (1).

As used herein, the term of "alkyl" refers to a saturated aliphatic hydrocarbon group. The alkyl moiety may be branched, straight chain, or include a cyclic portion. The point of attachment of an alkyl is at a carbon atom that is not part of a ring. Alkyl group may be a $C_1$-$C_{20}$ alkyl group, preferentially a $C_1$-$C_8$ alkyl group. Examples of an alkyl in the definition of Formula (1) are methyl, ethyl, n-propyl, isopropyl, n-butyl, t-butyl, amyl, hexyl, heptyl, octyl, and so on.

Suitable metal surface corrosion activators of Formula (1) may be monophenol compounds.

Preferably, suitable metal surface corrosion activators of Formula (1) are diphenol compounds.

Particularly useful metal surface corrosion activators of the present invention are catechol and its derivatives such as 2,3-dihydroxy benzoic acid (2,3-DBHA), 2,3-dihydroxy benzenesulfonic acid, 3,4-dihydroxy benzoic acid, 3,4-dihydroxy benzenesulfonic acid, catechol, 4-methyl catechol, 4-ethyl catechol, 4-isopropyl catechol or 4-tertio-butyl catechol or any combination thereof.

Preferably, the phenol compound as metal surface corrosion activator is used in a form of solution in a suitable solvent such as water.

Therefore, the present invention provides a formulation for metal surface corrosion comprising a compound of Formula (1) as a metal surface corrosion activator. Correspondingly, the present invention relates to use of a compound of Formula (1) in manufacture of a formulation for metal surface corrosion. The formulation of the present invention can be simply a solution of a compound of Formula (1) in a suitable solvent, for example an aqueous solution. As will be discussed below, other optional components can be included in the formulation of the present invention for different purposes.

Preferably, the metal surface corrosion activator is present in the range of about 0.1% to about 20% by weight of the formulation. In some embodiments, the metal surface corrosion activator is present in the range of about 0.1% to about 9% by weight. In some embodiments, the metal surface corrosion activator is in the range of about 0.1% to about 8% by weight. In some embodiments, the metal surface corrosion activator is in the range of about 0.1% to about 7% by weight. In some embodiments, the metal surface corrosion activator is in the range of about 0.1% to about 6% by weight. In some embodiments, the metal surface corrosion activator is in the range of about 0.1% to about 5% by weight. In some embodiments, the metal surface corrosion activator is in the range of about 0.1% to about 4% by weight. In some embodiments, the metal surface corrosion activator is in the range of about 0.1% to about 3% by weight. In some embodiments, the metal surface corrosion activator is in the range of about 0.1% to about 2% by weight. In some embodiments, the metal surface corrosion activator is in the range of about 0.5% to about 9% by weight. In some embodiments, the metal surface corrosion activator is in the range of about 0.5% to about 8% by weight. In some embodiments, the metal surface corrosion activator is in the range of about 0.5% to about 7% by weight. In some embodiments, the metal surface corrosion activator is in the range of about 0.5% to about 6% by weight. In some embodiments, the metal surface corrosion activator is in the range of about 0.5% to about 5% by weight. In some embodiments, the metal surface corrosion activator is in the range of about 0.5% to about 4% by weight. In some embodiments, the metal surface corrosion activator is in the range of about 0.5% to about 3% by weight. In some embodiments, the metal surface corrosion activator is in the range of about 0.5% to about 2% by weight. In some embodiments, the metal surface corrosion activator is in the range of about 1% to about 9% by weight. In some embodiments, the metal surface corrosion activator is in the range of about 1% to about 8% by weight. In some embodiments, the metal surface corrosion activator is in the range of about 1% to about 7% by weight. In some embodiments, the metal surface corrosion activator is in the range of about 1% to about 6% by weight. In some embodiments, the metal surface corrosion activator is in the range of about 1% to about 5% by weight. In some embodiments, the metal surface corrosion activator is in the range of about 1% to about 4% by weight. In some embodiments, the metal surface corrosion activator is in the range of about 1% to about 3% by weight. In some embodiments, the metal surface corrosion activator is in the range of about 1% to about 2% by weight.

In a preferable embodiment, the metal surface corrosion activator is present in the range of about 1% to about 5% by weight of the formulation.

The formulation may additionally comprise solvent, such as a dipolar aprotic solvent.

Examples of dipolar aprotic solvents useful for the formulation according to the invention include, but not limited to dimethyl sulfoxide, 2-pyrrolidone, N-substituted pyrrolidone such as N-methyl-2-pyrrolidone (NMP), dimethylacetamide, dimethyl formamide, pentanoic acid 5-(dimethylamino)-2-methyl-5-oxo-methyl ester and the like, or any combination thereof.

Preferably, the dipolar aprotic solvent is present in an amount of about 10% to about 50% by weight of the formulation, more preferably from about 20% to about 40%, and most preferably from about 30% by weight of the formulation.

When the dipolar aprotic solvent is included, the formulation according to the present invention may also comprise a water miscible organic solvent to form a homogeneous phase.

For this invention, "miscible" includes soluble.

In certain embodiments, the water miscible organic co-solvent may be glycol ether or a furfuryl alcohol. The glycol ethers may include glycol mono($C_1$-$C_6$)alkyl ethers and glycol di($C_1$-$C_6$)alkyl ethers, such as but not limited to, ($C_1$-$C_{20}$)alkane dials, ($C_1$-$C_6$)alkyl ethers, and ($C_1$-$C_{20}$)alkane dial di($C_1$-$C_6$)alkyl ethers. Examples of glycol ethers are to dipropylene glycol methyl ether, tripropylene glycol methyl ether, ethylene glycol monomethyl ether, ethylene glycol monoethyl ether, ethylene glycol monobutyl ether, ethylene glycol dimethyl ether, ethylene glycol diethyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol monobenzyl ether, diethylene glycol dimethyl ether, diethylene glycol diethyl ether, triethylene glycol monomethyl ether, triethylene glycol dimethyl ether, polyethylene glycol monomethyl ether, diethylene glycol methyl ethyl ether, triethylene glycol ethylene glycol monomethyl ether acetate, ethylene glycol monoethyl ether acetate, propylene glycol monomethyl ether, propylene glycol dimethyl ether, propylene glycol monobutyl ether, propylene glycol, monoproply ether, dipropylene glycol monomethyl ether, dipropylene glycol monopropyl ether, dipropylene glycol monoisopropyl ether, dipropylene glycol monobutyl ether, diproplylene glycol diisopropyl ether, tripropylene glycol monomethyl ether, 1-methoxy-2-butanol, 2-methoxy-1-butanol, 2-methoxy-2-methylbutanol, 1,1-dimethoxyethane and 2-(2-butoxyethoxy) ethanol, and mixtures thereof. More typical examples of glycol ethers are propylene glycol monomethyl ether, propylene glycol monopropyl ether, tri(propylene glycol) monomethyl ether and 2-(2-butoxyethoxy) ethanol. An example of a furfuryl alcohol is tetrahydrofurfuryl alcohol (THFA).

In certain embodiments, the water miscible organic solvent may be ethylene glycol, propylene glycol, benzyl alcohol, glycerol, dipropylene glycol monomethyl ether, diethylene glycol diethyl ether, diethylene glycol and mixtures thereof.

In a preferable embodiment, the water miscible organic solvent is diethylene glycol diethyl ether.

The water miscible organic solvent is preferably present in an amount of about 10 to about 50% by weight of the formulation, more preferably from about 20% to about 40% by weight, and most preferably about 30% by weight of the formulation.

The formulation of the invention may also comprise a solvent as a diester of formula (II):

$$R^1\text{—OOC-A-COO—}R^2,$$

wherein
$R^1$ and $R^2$, identical or different, are $C_1$-$C_{20}$ alkyl, aryl, alkyaryl, or arylalkyl groups, linear or branched, cyclic or non cyclic, and
A is a linear or branched divalent alkylene group, In the context of this formula, "alkyl" is understood to mean: a linear or branched hydrocarbon chain having from 1 to 20 carbon atoms and preferably from 1 or 2 to 10 carbon atoms; or a cyclic hydrocarbon group comprising from 3 to 8 carbon atoms, preferably a cyclopentyl or cyclohexyl group.

"Aryl" is understood to mean an aromatic mono- or polycyclic group, preferably a mono- or bicyclic group, comprising from 6 to 12 carbon atoms, preferably phenyl or naphthyl.

"Arylalkyl" is understood to mean a linear or branched hydrocarbon group carrying an aromatic monocyclic ring and comprising from 7 to 12 carbon atoms, preferably benzyl.

"Alkylaryl" is understood to mean an aromatic monocyclic group carrying an alkyl group.

The diester can be a mixture of different diesters of formula (II).

In formula (II) $R^1$ and $R^2$, identical or different are preferably selected from the group consisting of methyl, ethyl, n-propyl, isopropyl, n-butyl, isobutyl, n-hexyl, isooctyl, 2-ethylhexyl, cyclohexyl, phenyl and benzyl.

According to one embodiment of the invention, A is $C_3$-$C_{10}$ branched divalent alkylene. For example, A can be selected from the groups consisting of the following:
$A_{MG}$ of formula —CH(CH$_3$)—CH$_2$—CH$_2$—,
$A_{ES}$ of formula —CH(C$_2$H$_5$)—CH$_2$—, and
their mixtures.

In one embodiment the diester is:
CH$_3$—OOC—CH(CH$_3$)—CH$_2$—CH$_2$—COO—CH$_3$, or is a mixture of diesters comprising such a compound.

In one embodiment the diester is a mixture comprising diesters of the following formula (II'), (II'') optionally (II'''):

 (II')

 (II'')

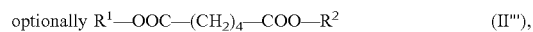 (II'''), wherein:
$A_{MG}$ is —CH(CH$_3$)—CH$_2$—CH$_2$—,
$A_{ES}$ is —CH(C$_2$H$_5$)—CH$_2$—.

In this embodiment $R^1$ and $R^2$ are preferably methyl groups.

The mixture of diesters can comprise:
from 70 to 95% by weight of diester of formule (II')
from 5 to 30% by weight of diester of formula (II''), and
from 0 to 10% by weight of diester of formule (II''').

An example of the useful diester-based solvent wherein A is branched is Rhodiasolv® IRIS, marketed by Rhodia.

Rhodiasolv® IRIS is a mixture of diesters comprising essentially (more than 80 wt %) of dimethyl ethylsuccinate and dimethyl 2-methylglutarate.

In one embodiment, A is a divalent alkylene group of formula (CH$_2$)$_r$, wherein r is an average number of from 2 to 4.

For example, the diester is a mixture of dimethyladipate (r=4), dimethylglutarate (r=3) and dimethylsuccinate (r=2), or a mixture of diethyladipate (r=4), diethylglutarate (r=3) and diethylsuccinate (r=2), or a mixture of diisobutyladipate (r=4), diisobutylglutarate (r=3) and diisobutylsuccinate (r=2).

For example the diester is a mixture comprising:
from 9 to 17% by weight of dimethyladipate,
from 59 to 67% by weight of dimethylglutarate, and
from 20 to 28% by weight of dimethylsuccinate.

An example of the useful diester-based solvent wherein A is linear is Rhodiasolv® RPDE, marketed by Rhodia.

Rhodiasolv® RPDE is a mixture of diesters comprising essentially (more than 70 wt %) of dimethylglutarate and dimethylsuccinate.

The diester which is used in the composition of the invention, can be prepared according to EP1991519.

According to another embodiment, the diester of formula (II) is a dialkylsuccinate, preferably dimethylsuccinate which can be prepared according to a chemical or biochemical process.

The formulation of the invention may also comprise a dioxolane derivative as solvent. Dioxolane derivatives may be those of Formula (III) as below:

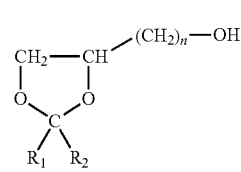

in which: $R_1$ and $R_2$, which are identical or different, represent hydrogen or a group or radical selected from the group comprising at least alkyl, alkenyl or phenyl radicals, and n is an integer 1, 2, 3, 4 or 5. Preferably n is 1 or 2.

In particular, $R_1$ and $R_2$ are radicals selected from the group comprising the methyl, ethyl, n-propyl, isopropyl or isobutyl radical.

Dioxolane derivatives of formula (III) may be as example: 2,2-dimethyl-1,3-dioxolane-4-methanol, also known by the name solketal, or 2,2-diisobutyl-1,-3-dioxolane-4-methanol, also known by the acronym IIPG for the synonym 1-isobutyl-isopropylidene glycerol.

The formulation may further comprise an organic base to adjust pH of the formulation to a suitable range. The formulation preferably has a pH from about 7 to about 10, more preferably from about 8 to about 9.

Suitable organic base can be chosen from a broad range of bases, such as amines, including but not limited to; monoethanolamine, aminoethoxyethanol, aminopropylmorpholine, monoethanolamine, N-methyl ethanolamine, N-ethyl ethanolamine, N,N-dimethylethanolamine, N,N-diethyl ethanolamine, N-methyl diethanolamine, N-ethyl diethanolamine, diethanolamine, triethanol amine, tertiary-butyldiethanol amine, isopropanolamine, 2-amino-1-propanol, 3-amino-1-propanol, 2-amino-1-butanol, isobutanolamine, 2-amino-2-ethoxypropanol, 2-amino-2-ethoxyethanol and mixtures thereof. In a preferable embodiment, the organic base is ethanolamine.

Preferably, the organic base is present from about 5% to about 20% by weight, more preferably 10% by weight of the formulation.

The present invention also provides a process of providing a clean metal surface by surface corrosion, comprising a step of contacting said metal surface with a metal surface corrosion activator of Formula (1). In the process, the formulation described above can be used.

The above suitable examples, preferred embodiments and range of amounts discussed in connection with the use and formulation of the present invention are also applicable to the process for providing a clean metal surface according to the present invention.

The present invention is useful for metal surface treatment of aluminum, copper, titanium, tungsten, other metals and/or alloys thereof. The present invention can find many applications. For example, in manufacture of electronic devices, the present invention will provide a clean and homogeneous metal surface for further processing.

The cleaning performance of the formulations of the present invention was assayed, for example, by using Electrochemical Test or by using Immerging test.

Electrochemical Test

Electrochemical Test performed to evaluate the performance of the chemical are based on a 3-electrode set-up. Chemical solution is placed in one jacketed reactor oil heated and thermally controlled at 60° C. Such reactor is equipped with a condenser to avoid any vapor release.

Metal sample (metal could be for example Aluminum or Copper alloy such as Al1100) to be tested is then partially immersed in the solution. Non-immersed part is covered with PTFE film and the sample is connected to a potentiometer Gamry 3000 as working electrode (WE).

A Calomel saturated electrode is connected as reference electrode (Ref) while a platinum electrode is connected as a counter electrode. Surface of the platinum electrode is large enough to avoid any current density limitation due to electron exchanges on CE.

Open circuit potential (OCP) is then recorded till potential stability and then, potentio-dynamic measurements are performed. Such measurements are done by application of a potential screening (WE vs Ref) at a scan rate of 10 mV/s coupled with a current density recording between WE and CE. Start of the potential screening is done at −200 mV/OCP and finished at +200 mV/OCP. Such measurements are done successively in both ways 3 times in order to identify any artefact or unexpected phenomena.

Current recordings are then exploited by Tafel representations in order to define the electron rate exchange at Open Circuit Potential. Using then exposed immersed samples areas, a specific current density due to electron exchanges related to a specific OCP is determined for each additive chemical tested.

This test leads to characterize the activation of the electron transfer due to additive chemical. Relationship observed between current density and OCP for each additive chemical is also a proof of activation of the electron exchange.

Immerging Test

Immerging tests are performed to evaluate the performance of the chemical with a long observation phenomenon, in which mainly loss on weight is recorded after a given time immerging in the cleaning solution.

Cleaning solution is prepared and poured into a bottle, then, a metal piece (Same type of metal was used as in above Electrochemical Test) is entirely immerged into this solution. The whole bottle is kept into an oven heated at 60° C. for usually one week.

In the end of the test, the metal piece is taken back from the solution, rinsed by water and dried.

After calculating the loss on weight before and after immerging, we transform it to the loss on thickness. We match the efficiency by the loss on thickness: the bigger loss on thickness, the more efficient in the surface corrosion.

The formulations containing phenol/diphenol derivatives as metal surface corrosion activators according to the present invention show good performance of metal surface corrosion.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. All such similar substitutes and modifications apparent to those skilled in the art are deemed to be within the spirit, scope and concept of the invention as defined by the appended claims.

In the following examples, all amounts were given in weight percent and add up to 100 weight percent.

Examples of formulations in the invention are given below. The abbreviations used herein are listed below.

2,3-DBHA: 2,3-dihydroxy benzoic acid

PC: catechol

TBC: 4-tertio-butyl catechol

4-MePC: 4-methyl-catechol

Example 1

The formulations disclosed herein were prepared by mixing the components together in a vessel until all solids have dissolved.

Following formulations were prepared.

TABLE 1

| Formulation | Metal Surface corrosion activator | Amount | Organic base (Ethanolamine) Amount | Water miscible organic solvent (diethylene glycol diethyl ether) Amount | Dipolar aprotic Solvent (N-methyl pyrrolidone) Amount | Water Amount |
|---|---|---|---|---|---|---|
| A | PC | 2% | 10% | 30% | 30% | To 100% |
| B | 2,3-DHBA | 1% | 10% | 30% | 30% | To 100% |
| C | 2,3-DHBA | 2% | 10% | 30% | 30% | To 100% |
| D | 4-MePC | 2% | 10% | 30% | 30% | To 100% |
| E | TBC | 0.1% | 10% | 30% | 30% | To 100% |
| F | TBC | 0.5% | 10% | 30% | 30% | To 100% |
| G | TBC | 1% | 10% | 30% | 30% | To 100% |
| H | PC | 1% | 10% | 30% | 30% | To 100% |

These were formulated with different kinds and amounts of metal surface corrosion activators.

Example 2

A series of the formulations prepared in Example 1 on Al samples were assayed by Electrochemical Test as discussed above. Results of the test are presented in FIG. 1 and Table 2 below.

FIG. 1 shows Tafel plots of blank (no phenol additive) and different metal surface corrosion activators, i.e. Formulation C (in which, the metal surface corrosion activator is 2,3-DHBA), Formulations F (in which, the metal surface corrosion activator is TBC), Formulation D (in which, the metal surface corrosion activator is 4-MePC) and Formulation A (in which, the metal surface corrosion activator is PC).

High current indicates strong metal dissolution rate, the potential (lower values) switch observed simultaneously along reduction slops is attributed to activation of electron transfer for WE (ex, dilution of metal).

The electrochemical potential versus current density for Al sample was measured in the formulations prepared in Example 1 to characterize the electron transfer thus the cleaning performance of them.

TABLE 2

| Formulation | Current/ µA | Potential (mV/CSE) | Area (cm²) | Current Density (µA/cm²) | Note |
|---|---|---|---|---|---|
| Blank | 0.8 | −250 | 6.25 | 0.13 | Values of |
| A | 9 | −320 | 4.50 | 2.00 | current density |
| B | 300 | −1100 | 6.00 | 50.00 | are |
| C | 1000 | −1230 | 6.75 | 148.15 | instantaneous |
| D | 11 | −400 | 5.50 | 2.00 | |
| E | 80 | −1080 | 4.25 | 18.82 | |
| F | 250 | −1120 | 4.75 | 52.63 | |
| G | 200 | −1140 | 6.25 | 32.00 | |

From the results as shown in Table 2, it can be seen that Formulations B, C (in which, the metal surface corrosion activator is 2,3-DHBA) show clearly the most interesting performance, followed with Formulations E, F and G (in which, the metal surface corrosion activator is TBC), Formulation D (in which, the metal surface corrosion activator is 4-MePC) and Formulation A (in which, the metal surface corrosion activator is PC).

The above results clearly show that the tested chemical additives are effective metal corrosion activators.

Example 3

A formulation prepared in Example 1 was assayed on Cu samples by Electrochemical Test as discussed above. Results of the test are presented in FIG. 2 and Table 3 below.

Figure 2:
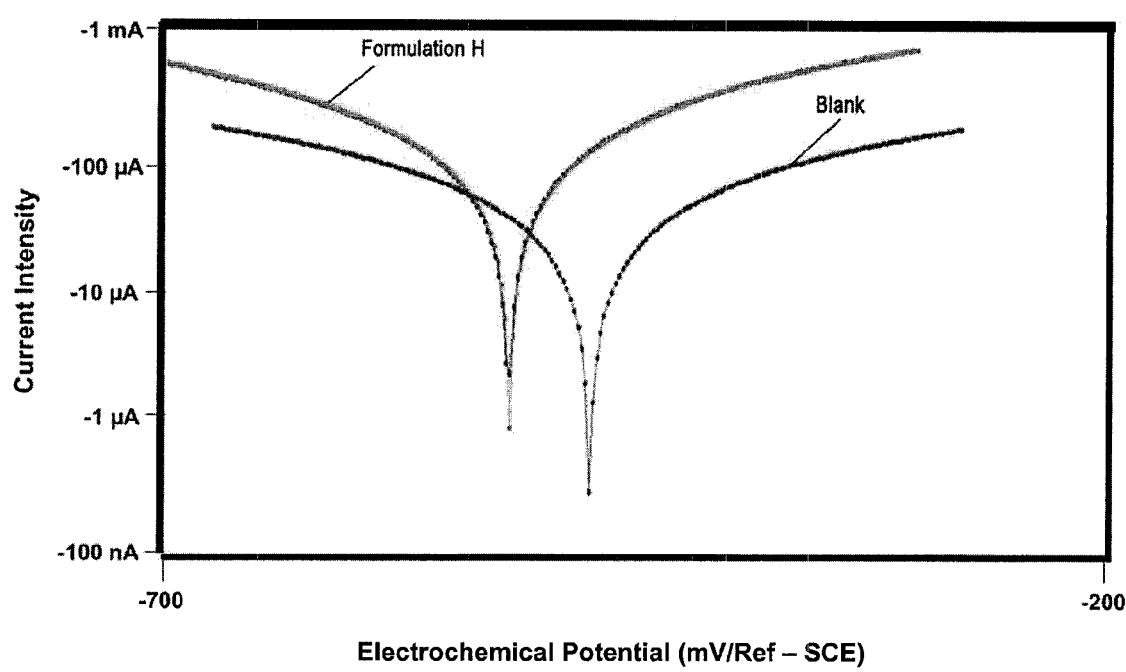
FIG. 2 shows the electro-chemical test results of Cu sample obtained with blank (no diphenol additive), Formulation H.

FIG. 2 shows Tafel plots of blank (no phenol additive) and a metal surface corrosion activator, i.e. Formulation H (in which, the metal surface corrosion activator is PC of 1%).

The electrochemical potential versus current density for Cu sample was measured in Formulation H prepared in Example 1 to characterize the electron transfer thus the cleaning performance of it.

TABLE 3

| Formulation | Current/ µA | Potential (mV/CSE) | Area (cm²) | Current Density (µA/cm²) | Note |
|---|---|---|---|---|---|
| Blank | 58 | −550 | 10.8 | 5.3 | Values of |
| H | 161 | −645 | 8.7 | 18.5 | current density are instantaneous |

From the results as shown in FIG. 2 and Table 3, it can be seen that the metal surface corrosion activators of the present invention are also effective on Cu.

Example 4

Figure 3:
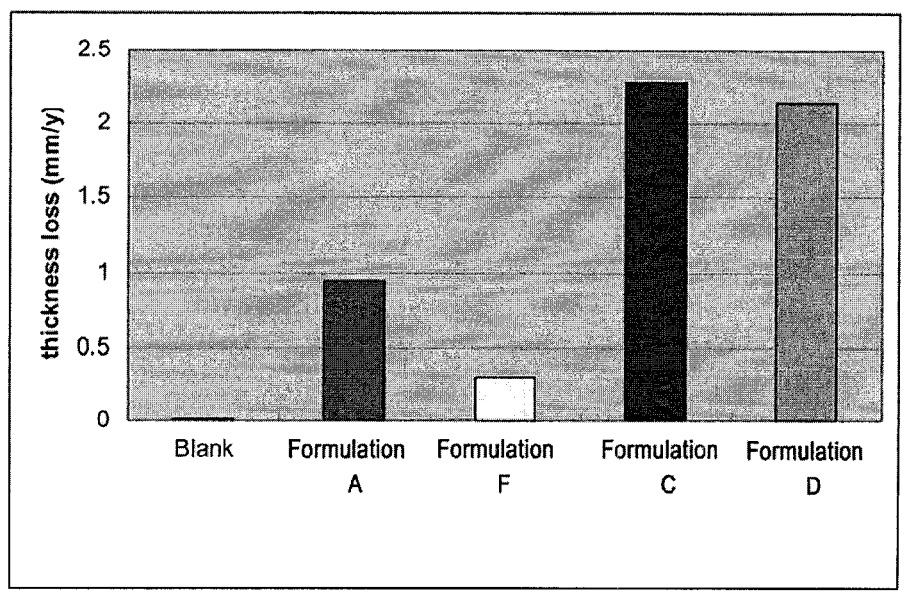
FIG. 3 shows the immerging test results of Al sample obtained with blank (no diphenol additive), Formulations A, C, D and F.

A series of the formulations prepared in Example 1 were test on Al samples by Immerging Test as described above. This is to characterize the loss on weight thus the cleaning performance of the corrosion activators. The metal samples were immerged for 7 days before measuring the weight loss. The test results are shown in FIG. 3, which are reported as thickness loss in mm per year. It is interesting to note that the rates of thickness loss as found in connection with the phenol compounds of the present invention are good for metal surface cleaning without over-corrosion of the metal surface.

In FIG. 3, the immerging test results are presented in bar graphs. In comparison with the blank control test, significant thickness loss of Al was observed in tests using PC, TBC, 2,3-dihydroxy benzoic acid and 4-methyl catechol. From the appearance of the treated metal samples, homogeneous metal corrosion was obtained by removing all the defaults of the metal surfaces. Interestingly, in comparison with Formulation A (in which, the metal surface corrosion activator is PC of 2%), Formulation C (in which, the metal surface corrosion activator is 2,3-DHBA of 2%) and Formulation D (in which, the metal surface corrosion activator is 4-MePC of 2%) have achieved much improved performance.

What is claimed is:

1. A method for providing a clean metal surface by surface corrosion, comprising:
    contacting a metal surface with a formulation comprising a compound of Formula (1) as a metal surface corrosion activator,

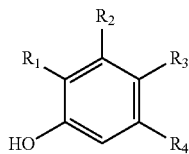

Formula (1)

wherein each of $R_1$, $R_2$ and $R_4$ in said Formula (1) is selected from the group consisting of hydrogen, hydroxyl group, alkyl group, sulfonic group, and carboxylic group; and $R_3$ in said Formula (1) is selected from the group consisting of hydrogen, alkyl group, sulfonic group, and carboxylic group;
thereby corroding the metal surface.

2. The method according to claim 1, wherein said compound of Formula (1) is a monophenol compound or diphenol compound.

3. The method according to claim 1, wherein said compound of Formula (1) is selected from the group consisting of catechol; 2,3 dihydroxy benzoic acid; 4-methyl catechol; and 4-tertio-butyl catechol.

4. The method according to claim 1, wherein said compound of Formula (1) is present in an amount of about 0.1% to about 20% by weight of said formulation.

5. The method according to claim 1, wherein said formulation further comprises water.

6. The method according to claim 1, wherein said formulation further comprises a dipolar aprotic solvent.

7. The method according to claim 1, wherein said formulation further comprises a water miscible manic solvent.

8. The method according to claim 1, wherein said formulation further comprises a diester of formula (II):

$R^1$—OOC-A-COO—$R^2$, wherein:
    $R^1$ and $R^2$, identical or different in said Formula (II), are $C_{1-20}$ alkyl, aryl, alkyaryl, or arylalkyl groups, which are linear or branched, and which are cyclic or non-cyclic, and
    A in said Formula (II) is a linear or branched divalent alkylene group.

9. The method according to claim 1, wherein said formulation further comprises a dioxolane derivative of Formula (III):

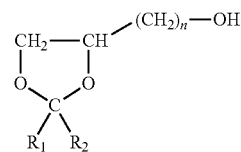

wherein R1 and R2, which are identical or different in said Formula (III), represent hydrogen or a group or radical selected from the group consisting of alkyl radicals, alkenyl radicals, and phenyl radicals, and n in said Formula (III) is an integer 1, 2, 3, 4 or 5.

10. The method according to claim 1, wherein said formulation further comprises an organic base to adjust pH of said formulation.

11. A process for providing a clean metal surface by surface corrosion, comprising a step of contacting a metal surface with a metal surface corrosion activator of Formula (1):

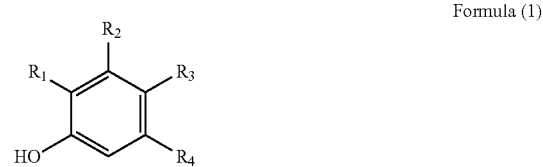

Formula (1)

wherein each of R, $R_2$ and $R_4$ in said Formula (1) is selected from the group consisting of hydrogen, hydroxyl group, alkyl group, sulfonic group, and carboxylic group; and wherein $R_3$ in said Formula (1) is selected from the group consisting of hydrogen, alkyl group, sulfonic group, and carboxylic group.

12. The process according to claim 11, wherein said compound of Formula (1) is a monophenol compound or diphenol compound.

13. The process according to claim 11, wherein said compound of Formula (1) is selected from the group consisting of catechol; 2,3 dihydroxy benzoic acid; 4-methyl catechol; and 4-tertio-butyl catechol.

14. The process according to claim 11, wherein said compound of Formula (1) is used in a form of a formulation for metal surface corrosion.

15. The process according to claim 14, wherein said compound of Formula (1) is present in an amount of about 0.1% to about 20% by weight of said formulation.

16. The process according to claim 14, wherein said formulation further comprises water.

17. The process according to claim 14, wherein said formulation further comprises a dipolar aprotic solvent.

18. The process according to claim 14, wherein said formulation further comprises a water miscible organic solvent.

19. The method according to claim 1, wherein said formulation further comprises a water miscible organic solvent selected from the group consisting of ethylene glycol, propylene glycol, benzyl alcohol, glycerol, dipropylene glycol monomethyl ether, diethylene glycol diethyl ether, diethylene glycol, and mixtures thereof.

20. The method according to claim 10, wherein said organic base in said formulation is selected from the group consisting of amines.

* * * * *